US008551718B2

(12) United States Patent
Ahmad et al.

(10) Patent No.: US 8,551,718 B2
(45) Date of Patent: Oct. 8, 2013

(54) FUNCTIONAL ASSAY FOR 5-HT2A, HISTAMINE H1 OR ADRENERGIC ALPHA 1B RECEPTORS

(75) Inventors: Ishtiyaque Ahmad, Hyderabad (IN); Reddy Venkat Mekala, Hyderabad (IN); Reddy Muddukrishna Chillakur, Hyderabad (IN); Ramkumar Subramaniam, Hyderabad (IN); Jyothsna Ravula, Hyderabad (IN); Sriramachandra Murthy Patnala, Hyderabad (IN); Ramakrishna Nirogi, Hyderabad (IN); Venkateswarlu Jasti, Hyderabad (IN)

(73) Assignee: Suven Life Science Limited, Hyderabad (IN)

( * ) Notice: Subject to any disclaimer, the term of this patent is extended or adjusted under 35 U.S.C. 154(b) by 0 days.

(21) Appl. No.: 13/519,556

(22) PCT Filed: Mar. 31, 2010

(86) PCT No.: PCT/IN2010/000209
§ 371 (c)(1),
(2), (4) Date: Aug. 20, 2012

(87) PCT Pub. No.: WO2011/080750
PCT Pub. Date: Jul. 7, 2011

(65) Prior Publication Data
US 2012/0315657 A1 Dec. 13, 2012

(30) Foreign Application Priority Data
Dec. 29, 2009 (IN) .......................... 3194/CHE/2009

(51) Int. Cl.
*G01N 33/567* (2006.01)
*C12Q 1/66* (2006.01)

(52) U.S. Cl.
USPC ............................................ 435/7.21; 435/8

(58) Field of Classification Search
USPC .................................................. 435/8, 7.21
See application file for complete search history.

(56) References Cited

FOREIGN PATENT DOCUMENTS
WO          0034783 A1    6/2000

OTHER PUBLICATIONS

George et al. Functional Coupling of Endogenous Serotonin (5-HT1B) and Calcitonin (C1A) Receptors in CHO Cells to a Cyclic-AMP Responsive Luceferase Reporter Gene; Journal of Neurochemistry, vol. 69 (1997) pp. 1278-1285.*
Deschamps, Jacqueline et al, "Identification of a Transcriptional Enhancer Element Upstream from the ProtoOncogene fos", Science, American Association for the Advancement of Science, vol. 230, No. 4730, Dec. 6, 1985, pp. 1174-1177.
Montminy, Marc R. et al, "Identification of a Cyclic-AMP-Responsive Element within the Rat Somatostatin Gene", Proc. Natl. Acad. Sci, Biochemistry, USA, vol. 83, Sep. 1986, pp. 6682-6686.
Angel, Peter et al, "Phorbol Ester-Inducible Genes Contain a Common Cis Element Recognized by a TPA-Modulated Trans-Acting Factor", Cell, vol. 49, 1987, pp. 729-739.
Fisch, Tobe M. et al, "An AP1-binding site in the c-fos gene can mediate induction by epidermal growth factor and 12-O-tetradecanoyl phorbol-13-acetate", Molecular and Cellular Biology, American Society for Microbiology, vol. 9, No. 3,1989, pp. 1327-1331.
Konig, M. et al, "Method for Identifying Ligands That Bind to Cloned Gs- or Gi Coupled Receptors", Molecular and Cellular Neurosciences, vol. 2, 1991, pp. 331-337.
Chen, Wenbiao, "A Colorimetric Assay for Measuring Activation of Gs- and Gq-Coupled Signaling Pathways", Academic Press, Inc., Analytical Biochemistry, Academic Press, Inc., vol. 226, 1995, pp. 349-354.
European Patent Office, International Search Report, International Search Authority, PCT International Patent Application No. PCT/IN2010/000209, Sep. 17, 2010.
Castanon M. J. et al; "Functional Coupling of Human Adenosine Receptors to a Ligand-Dependent Reporter Gene System", Biochemical and Biophysical Research Communications, Academic Press Inc., Orlando, FL, US LNKD, vol. 198, No. 2, Jan. 31, 1994, pp. 626-631.
George S. E. et al; "Functional Analysis of the D2L Dopamine Receptor Expressed in a cAMP-Responsive Luciferase Reporter Cell Line", Biochemical Pharmacology, Jul. 1, 1998, vol. 56, No. 1, pp. 25-30.
Himmler A. et al; "Functional Testing of Human Dopamine D1 and D5 Receptors Expressed in Stable Camp-Responsive Luciferase Reporter Cell Lines", Journal of Receptor Research, New York, NY, vol. 13, No. 1/04, Jan. 1, 1993, pp. 79-84.
Stratowa Christian et al; "Use of a Luciferase Reporter System for Characterizing G-Protein-Linked Receptors", Current Opinion in Biology, vol. 6, No. 5, 1995, pp. 574-581.
Jiang Nan et al; "Identification of Human Dopamine D1-Like Receptor Agonist Using a Cell-Based Functional Assay", ACTA Pharmacologica Sinica, Oct. 2005, vol. 26, No. 10, pp. 1181-1186.
Monica Gallego et al; "Alpha-1 Adrenoceptors Stimulate a G-alpha s Protein and Reduce the Transient Outward K Current via a cAMP/PKA Mediated Pathway in the Rat Heart", Am J Physiol Cell Physiol 288, pp. C577-C585, 2005.
Knut Kotarsky et al; "A Chimeric Reporter Gene Allowing for Clone Selection and High Throughput Screening of Reporter Cell Lines Expressing G-Protein Coupled Receptors", Analytical Biochemistry 288, pp. 209-215, 2001.
C. Stratowa et al; "Functional Characterization of the Human Neurokinin Receptors NK1, NK2, and NK3 Based on a Cellular Assay", J. of Receptor & Signal Transduction Research, 15(1-4), pp. 617-630, 1995, abstract only.
U. Weyer et al; "Establishment of a Cellular Assay System for G Protein-Linked Receptors: Coupling of Human NK2 and 5-HT2 Receptors to Phospholipase C Activates a Luciferase Reporter Gene", Receptors and Channels, vol. 1, pp. 193-2001.
European Patent Office, International Preliminary Report on Patentability, International Preliminary Examining Authority, PCT International Patent Application No. PCT/IN2010/000209, May 4, 2012.

\* cited by examiner

*Primary Examiner* — Susan Hanley
*Assistant Examiner* — Paul Martin
(74) *Attorney, Agent, or Firm* — Iphorgan, Ltd.

(57) ABSTRACT

The present invention provides novel functional assay for 5-$HT_{2A}$, histamine H1 or adrenergic alpha 1b receptors, by measuring intracellular cyclic adenosine monophosphate (cAMP) levels utilizing reporter gene driven cell based assay. The novel assay provides both binding affinity as well as mode of action of compounds in a single set. The novel assay of the invention is useful in identification of compounds acting through 5-$HT_{2A}$, histamine H1 or adrenergic alpha 1b receptors. Furthermore, the assay offers utility in categorizing compounds in to agonist, partial agonist, inverse agonist and antagonist classes. The novel assay can be scaled up to any high throughput format.

3 Claims, 6 Drawing Sheets

FUNCTIONAL ASSAY FOR 5-HT2A, HISTAMINE H1 OR ADRENERGIC ALPHA 1B RECEPTORS

CROSS-REFERENCE TO RELATED APPLICATIONS

This application claims the benefit of International Application No. PCT/IN2010/000209, filed on Mar. 31, 2010, which in turn claims priority to Indian Patent Application No. 3194/CHE/2009, filed Dec. 29, 2009, the contents of which are both hereby incorporated by reference.

FIELD OF INVENTION

The present invention describes establishment of a cell based functional assay for 5-HT$_{2A}$, histamine H1 or adrenergic alpha 1b receptors, by determining the level of intracellular cAMP levels utilizing reporter gene driven cell based assay. The novel assay described in the current invention, combines features of binding and functional mode in a single type of experimental set up which offers both binding affinity as well as mode of action of compounds interacting with any 5-HT$_{2A}$, histamine H1 or adrenergic alpha 1b receptors in a single set. The novel assay of the invention is useful in identification of compounds acting through 5-HT$_{2A}$, histamine H1 or adrenergic alpha 1b receptors and their further categorization based on the mode of action. The assay may find high utility in screening of new chemical entities for identification of novel drugs acting through 5-HT$_{2A}$, histamine H1 or adrenergic alpha 1b receptors. Moreover, the novel assay can also be utilized in exploring the mode of action of established and known drugs and assignment of their pharmacological properties.

BACKGROUND OF THE INVENTION

GPCRs also known as seven-transmembrane domain receptors comprise a large protein family of transmembrane receptors that sense molecules outside the cell and activate inside signal transduction pathways and ultimately cellular responses. GPCRs are involved in various physiological functions as well as many diseases, and are also the target of around half of all modem medicinal drugs. There are two principal signal transduction pathways involving the GPCRs: cAMP signal pathway and Phosphatidylinositol signal pathway.

The cytoplasmic tail region of GPCRs interacts to one of the three main classes of G proteins. G proteins are composed of a common βγ subunit and a specific α subunit. The role of the α subunit is well known for translating the extracellular cues to intracellular responses. G proteins are mainly classified into three categories based on the nature of their subunits. G proteins containing Gαs or Gαi subunits enhance or reduce the cAMP level respectively upon receptor stimulation through adenylate cyclase enzyme. In contrast, G proteins comprising Gαq subunit mobilize intracellular calcium ions upon activation of the receptor through a membrane bound phospholipase C enzyme. In recent years, Gβγ subunits turned out to be more than a silent partner. They too transmit the message through activation of ERK-MAPK pathways.

The molecular diversity of GPCR-mediated signal transduction pathway complicates the configuration of a common functional assay. The development of high through-put functional assays for GPCRs would greatly enhance the ability to discover and develop novel agonists and antagonists to this important superfamily of pharmaceutical targets. One approach for developing a high through-put functional GPCR assay is the use of reporter gene assays. Reporter gene constructs couple transcriptional enhancers that are regulated by various intracellular second messengers with appropriate promoter and reporter gene elements to produce a surrogate signal transduction system responsive to signaling pathways activated by various hormone receptors (Deschamps, Science, 1985 230:1174-7; Montminy, Proc. Nail. Acad Sci USA, 1986 83:6682-6686; Angel, Cell, 1987, 49:729-39; Fisch, Mol. Cell. Biol, 1989 9:1327-31). With the appropriate choice of transcriptional enhancers, promoters, and reporter genes, non-radiometric functional assays have been configured for Gαs coupled GPCRs (Konig, Mol. Cell. Neurosciences, 1991, 2:331-337; Chen, Anal. Biochemistry, 1995, 226: 349-354) and Gαq coupled GPCRs (Weyer, Receptor and Channels, 1993 1:193-200) that are amenable to high through-put screening technology.

Earlier, some assays have been developed for the identification of GPCRs. However, some disadvantages are associated with the traditional radioligand binding assay and FLIPR based functional assays. In traditional binding assay a) hazardous radioactive ligands are used; b) the mode of action of a molecule needs to be further investigated using a separate radioactive or cell based functional assay. In the FLIPR based functional assay (European patent application: EP1310800), fluorescent counts are measured within 5 seconds of compound injection which may not be sufficient to bring the compound in equilibrium with the receptor. As a result of shorter incubation of compounds in FLIPR assay, important compounds may be missed out or artefactual values may be generated.

In order to overcome the above mentioned disadvantages, we have developed novel functional assay for 5-HT$_{2A}$, histamine H1 or adrenergic alpha 1b receptors based on measurement of intracellular cAMP levels by measuring reporter gene activity:

a) which eliminates the usage of hazardous radioactive ligands. Thus an environmental friendly approach can be implemented to identify novel compounds.

b) mode of action (agonist or antagonist) as well as binding affinity of the ligand (pK$_b$ or pEC50) are derived from the same experiment.

c) compounds are incubated for few hours to bring them in equilibrium with the receptor. Longer incubation period in reporter gene format is required to have a sustained activation of the receptor leading to the synthesis of cAMP and induction of the reporter gene.

Thus, the reporter gene based assay may be more in line with the physiological conditions wherein the drug is allowed to interact with the target receptor in the body.

SUMMARY OF INVENTION

In one aspect, the present invention provides a novel functional assay method for identification of compounds acting through GPCRs, which comprises:

a) transfecting chinese hamster ovary (CHO) cells with specific 5-HT$_{2A}$, histamine H1 of adrenergic alpha 1b receptors constructs along with express of reporter gene using Lipofectamine® 1-Propanaminium, N-(3-[(4[(3-aminopropyl) amino) butyl) amino) propyl) amino)-3-oxopropyl)-N,N-dimethyl-2,3-bis(((9z)-1-oxo-9-octadecenyl)oxy)-, 2,2,2-trifluoroacetate (1:1), mixt. with 1-(((2-aminoethoxy) hydroxyphosphinyl)oxy)methyl)-1,2-ethanediyl di-(9z)-9-octadecenoate and cultured in suitable medium containing selection antibiotics;

In one aspect, the present invention provides a novel functional assay method for identification of compounds acting through $5-HT_{2A}$, histamine H1 or adrenergic alpha 1b receptors, which comprises:
- b) picking up individual colonies exhibiting maximum luciferase activity with both forskolin as well as the agonist and analyzing the expression of said $5-HT_{2A}$, histamine H1 or adrenergic alpha 1b receptors;
- c) plating recombinant CHO cells in a microtitre plate and cultured;
- d) incubating said recomninant cells with increasing concentration of compounds at 37° C. in $CO_2$ incubator for evaluation of compounds in antagonist mode and agonist mode of $5-HT_{2A}$, histamine H1 or adrenergic alpha 1b receptors;
- e) after incubation of the cells was over, removing the medium and washing the cells with buffer and lysed in the lysis buffer;
- f) measuring CRE-Luc reporter gene activity in individual wells.

In another aspect, total RNA isolated from each cell line was used in the cDNA synthesis.

In further aspect, radioligand binding and competition assays were performed with membranes prepared from the recombinant CHO cell lines.

In yet another aspect, mode of action (agonist or antagonist) as well as binding affinity of the ligand ($pK_b$ or pEC50) is derived from the same experiment.

BRIEF DESCRIPTION OF DIAGRAMS

DETAILED DESCRIPTION OF INVENTION

Luciferin, T4 DNA Ligase, high fidelity Taq polymerase, superscript reverse transcriptade, mammalian vector pcDNA3.1, CRE-Luc reporter gene, cell culture media, sera, radioligands Ketanserin Hydrochloride [ethylene-$^3$H] 60-90 Ci/mmol, Prazosin [7-methoxy-$^3$H] 70-87 Ci/mmole, Pyrilamine [pyridinyl 5-$^3$H], (Mepyramine) 20-30 Ci/mmol, scintillation proximity assay beads, Human $5-HT_{2A}$ cDNA clone, Adrenergic alpha1b cDNA clone, all other DNA restriction enzymes, modification enzymes, all other reagents and common chemicals were purchased from well known suppliers.

Human $5-HT_{2A}$ cDNA clone was amplified by polymerase chain reaction (PCR) using gene specific primers. Adrenergic $alpha_{1b}$ cDNA clone was amplified by PCR using gene specific primers. Human histamine $H_1$ cDNA was generated by reverse transcription using total RNA isolated from HepG2, 1MR32, HEK293 and CaCo2 cell lines and gene specific reverse primers. The cDNA was amplified by PCR using gene specific primers using high fidelity Taq DNA polymerase. Amplified DNA was cloned in to mammalian expression vector pcDNA 3.1. The authenticity of the cloned genes was determined by restriction analysis and nucleotide sequencing.

EXAMPLE 1

Expression of the RNA in Recombinant CHO Cells

Total RNA from recombinant or control CHO cells were isolated using TRI reagent (Sigma) as recommended. The quality of each RNA sample was analyzed by agarose gel electrophoresis. Total RNA from each cell line was used in the cDNA synthesis by reverse transcription using Superscript Reverse Transcriptase and gene specific reverse primers for $5-HT_{2A}$, $Alpha_{1b}$, $H_1$ and β-actin genes. PCR was performed on each cDNA sample using gene specific forward and reverse primers. Samples were separated on 1% agarose gel and visualized after Ethidium bromide staining.

Figure 1:
FIG. 1 shows expression of the RNA in recombinant CHO cells.

As evident from FIG. 1, human $5-HT_{2A}$ is exclusively expressed in CHO cells transfected with human $5-HT_{2A}$ gene (CHO-$5HT_{2A}$) and not in control and other transfected cells. Similarly human histamine $H_1$ or adrenergic $alpha_{1b}$ mRNA are exclusively expressed in CHO cells transfected with human $H_1$ or $\alpha_{1b}$ cDNA (CHO-$H_1$ or CHO-$\alpha_{1b}$) respectively. β-actin mRNA was also reverse transcribed in the same set of assays using a gene specific reverse primer. The cDNA from each of the cell line was amplified using β-actin specific forward and reverse primers. Presence of a band corresponding to β-actin fragment in FIG. 1 demonstrated the presence and good quality of the RNA in each preparation.

EXAMPLE 2

Stimulation of Luciferase Reporter Gene in CHO Cells

Each recombinant CHO cell line was plated in 96 well white with clear bottom plates. The ligands as indicated were added to a final concentration of 10 μM. The luciferase activity was measured in individual wells using luciferin substrate in Perkin Elmer luminometer. The basal luciferase activity for each cell line was assigned an arbitrary value of 1. Fold stimulation with each ligand was determined in relation to the basal luciferase activity.

Figure 2:
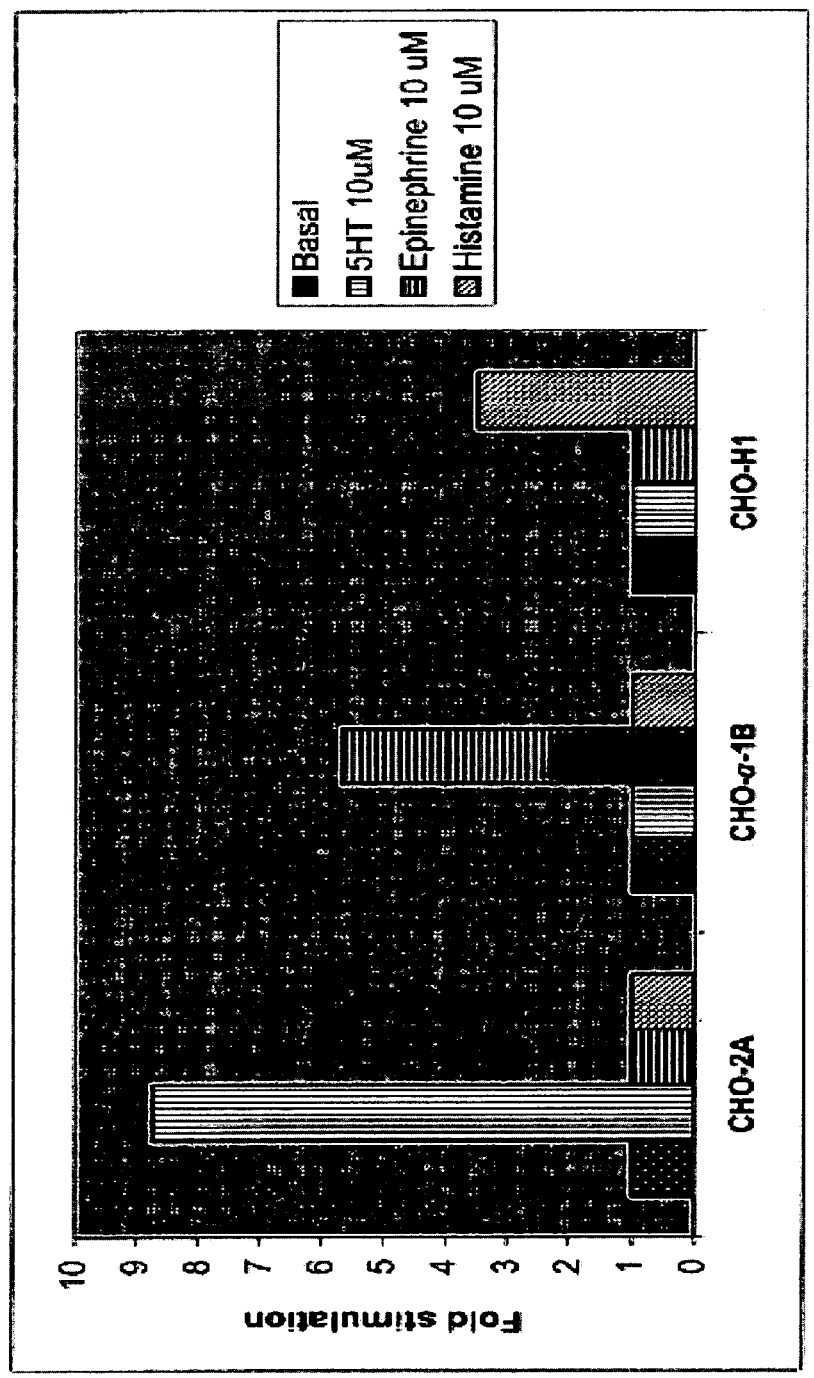
FIG. 2 shows stimulation of luciferase reporter gene in CHO cells expressing human $5-HT_{2A}$, adrenergic $Alpha_{1b}$ or Histamine $H_1$ receptors.

The assay was also utilized to investigate the specificity of various ligands and authenticity of the generated cell lines in this assay. As evident from FIG. 2, serotonin at a concentration of 10 μM demonstrated about nine fold induction of luciferase activity in CHO-$5HT_{2A}$ cells. However, histamine and epinephrine at the same concentration did not show a significant induction of luciferase activity in CHO-$5HT_{2A}$ cells. Similarly, epinephrine at a concentration of 10 μM induced the expression of luciferase activity to about six fold in CHO-$\alpha_{1b}$ cells. As expected, CHO-$\alpha_{1b}$ cells did not respond to the treatment with 10 μM serotonin or histamine (FIG. 2). CHO-$H_1$ cells exhibited about three fold enhanced expression of luciferase enzyme with 10 μM histamine. Epinephrine and serotonin (10 μM each) did not show any effect on the level of luciferase activity in CHO-$H_1$ cells. A strong induction in luciferase activity was observed in all the three recombinant cell lines upon treatment with forskolin.

EXAMPLE 3

Ligands Stimulate the Specific Receptor in a Dose Dependent Manner

To further confirm the single dose effect of specific agonists on the recombinant CHO cell lines, a dose response effect with different agonists was measured. Each recombinant cell line was treated with individual agonists from 0.1 nM to 10,000 nM and luciferase activity was measured by using luciferin substrate in Victor Light Luminometer from Perkin Elmer. The agonist stimulated luciferase activity in the absence of a compound was assigned a value of 100% while basal luciferase activity was assigned a value of 0%. Rest of the luminescent values obtained for compounds at various doses were calculated with reference to stimulated and basal luciferase activities. Data was analyzed using Graphpad software.

Figure 3:
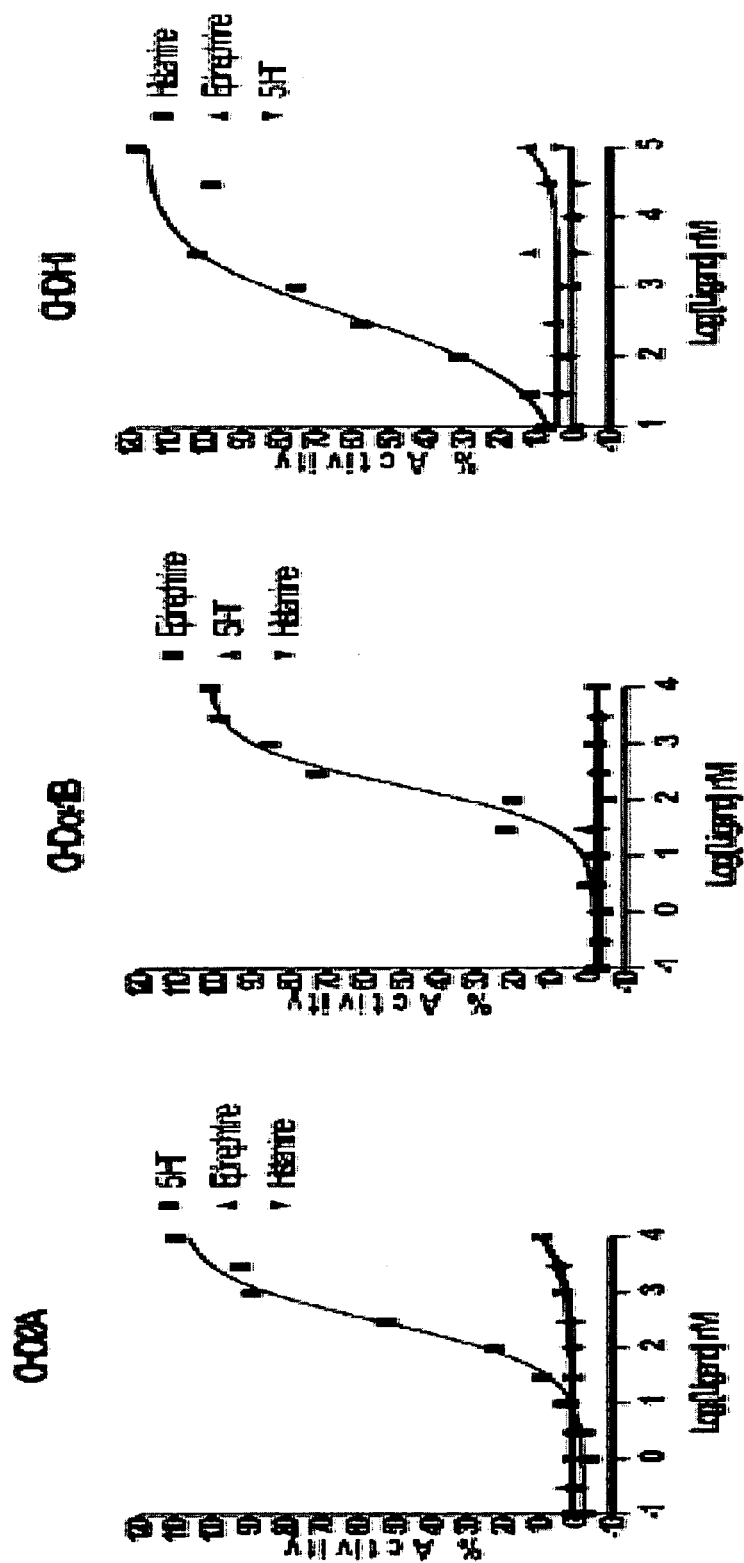
FIG. 3 shows ligands stimulate the specific receptor in a dose dependent manner.

Serotonin showed a specific dose response effect on the expression of luciferase activity in CHO-5HT$_{2A}$ cells (FIG. 3). A pEC$_{50}$ value of 6.6 for serotonin in the assay was determined (Table 1). Epinephrine and histamine did not show the induction of luciferase activity in CHO-5HT$_{2A}$ cells up to the highest dose tested (FIG. 3). 5-HT$_{2A}$ receptor is not reported to couple to G$\alpha$s containing G protein or stimulate cAMP production under any experimental conditions reported so far. 5-HT$_{2A}$ receptor is well established to couple to G$\alpha$q containing G protein (Raymond J R. Mukhin Y V, Gelasco A, Turner I, Collinsworth G, Gettys T W, Grewal J S, Garnovskaya M N: Multiplicity of mechanisms of serotonin receptor signal transduction. Pharmacol Ther 2001, 92: 179-2 12). Some reports also suggest inhibition of cAMP accumulation upon activation of 5-HT$_{2A}$ receptor (Garnovskaya M N, Nebigil C G, Arthur J M, Spurney R F, Raymond J R: 5-hydroxytryptamine 2A receptors expressed in rat renal mesangial cells inhibit cyclic AMP accumulation. Mol Pharmacol 1995, 48: 230-237). A range of pK$_i$ values from 8.4 to 6.0 are reported for serotonin in 5-HT$_{2A}$ radioligand binding assays in IUPHAR database. The pEC$_{50}$ value determined in the current investigations falls in the middle of the reported range.

CHO-$\alpha_{1b}$ cells showed a robust dose response with increasing concentrations of epinephrine from 0.1 to 10000 nM as evident from the level of luciferase activity observed (FIG. 3). The treatment of recombinant cells with epinephrine provided a pEC$_{50}$ value of 7.3 (Table 1). pEC$_{50}$ values of 7.3 and 6.6 for calcium mobilization and cAMP accumulation respectively are reported for CHO cells expressing human adrenergic alpha1b receptor upon treatment with norepinephrine (Horie K, Itoh H, Tsugimoto G: Hamster $\alpha_{1b}$-adrenergic receptor directly activates Gs in the transfected chinese hamster ovary cells. Mol Pharmacol 1995, 48: 392-400), (Gallego M, Setien R, Puebla L, Boyano-Adanez MdC, Arilla E, Casis O: $\alpha_1$-adrenoceptors stimulate a G$\alpha$s protein and reduce the transient outward K$^+$ current via a cAMP/PKA-mediated pathway in the rat heart. Am J Physiol Cell Physiol 2004, 288: C577-C585). CHO-$\alpha_{1b}$ cells did not respond to histamine or serotonin treatment as evident from basal level of luciferase activity observed at the highest concentration of the ligand tested (FIG. 3).

Following on the same pattern, CHO-H$_1$ cells were treated with increasing concentrations (1 to 100,000 nM) of histamine. A dose proportionate increase in luciferase activity was observed in CHO-H$_1$ cells treated with histamine but not with serotonin or epinephrine. Histamine showed a pEC$_{50}$ value of 6.0 in this assay. Moniri et. al. reported a pEC$_{50}$ value of 5.8 in a cAMP accumulation assay in CHO cells expressing human histamine H$_1$ receptor upon treatment with histamine (Moniri N H, Covington-Strachan D, Booth R G: Ligand-directed functional heterogeneity of histamine H1 receptors: novel dual function ligands selectively activate and block H1-mediated phospholipase C and adenylyl cyclase signaling. J Pharmacol Exp Ther 2004; 311: 274-281) Overall, the values reported in the present assay are well in agreement with the published values generated using different strategies for three receptors under investigation.

TABLE 1

| | pEC$_{50}$ values | | |
| Compounds | CHO-5HT$_{2A}$ | CHO-$\alpha_{1b}$ | CHO—H$_1$ |
| --- | --- | --- | --- |
| Serotonin | 6.6 ± 0.1 | <5 | <5 |
| Epinephrine | <5 | 7.0 ± 0.3 | <5 |
| Histamine | <5 | <5 | 6.0 ± 0.1 |

EXAMPLE 4

Blockade of Reporter Gene Expression by Antagonists

Once we observed an induction of reporter gene activity in all recombinant cell lines evaluated in a agonist and dose dependent manner, it was of interest to determine whether the activity was blocked by various known antagonists. A number of compounds already demonstrated to antagonize some or all of the receptors under investigation were selected for the current study. Vehicle or selected compounds (10 μM concentrations) were incubated along with 10 μM of specific agonist with the cells and luciferase activity was measured by Victor Light Luminometer from Perkin Elmer. A detailed evaluation of various compounds in specific cell lines is presented in FIG. 4.

EXAMPLE 5

Dose Response Study

Figure 5:
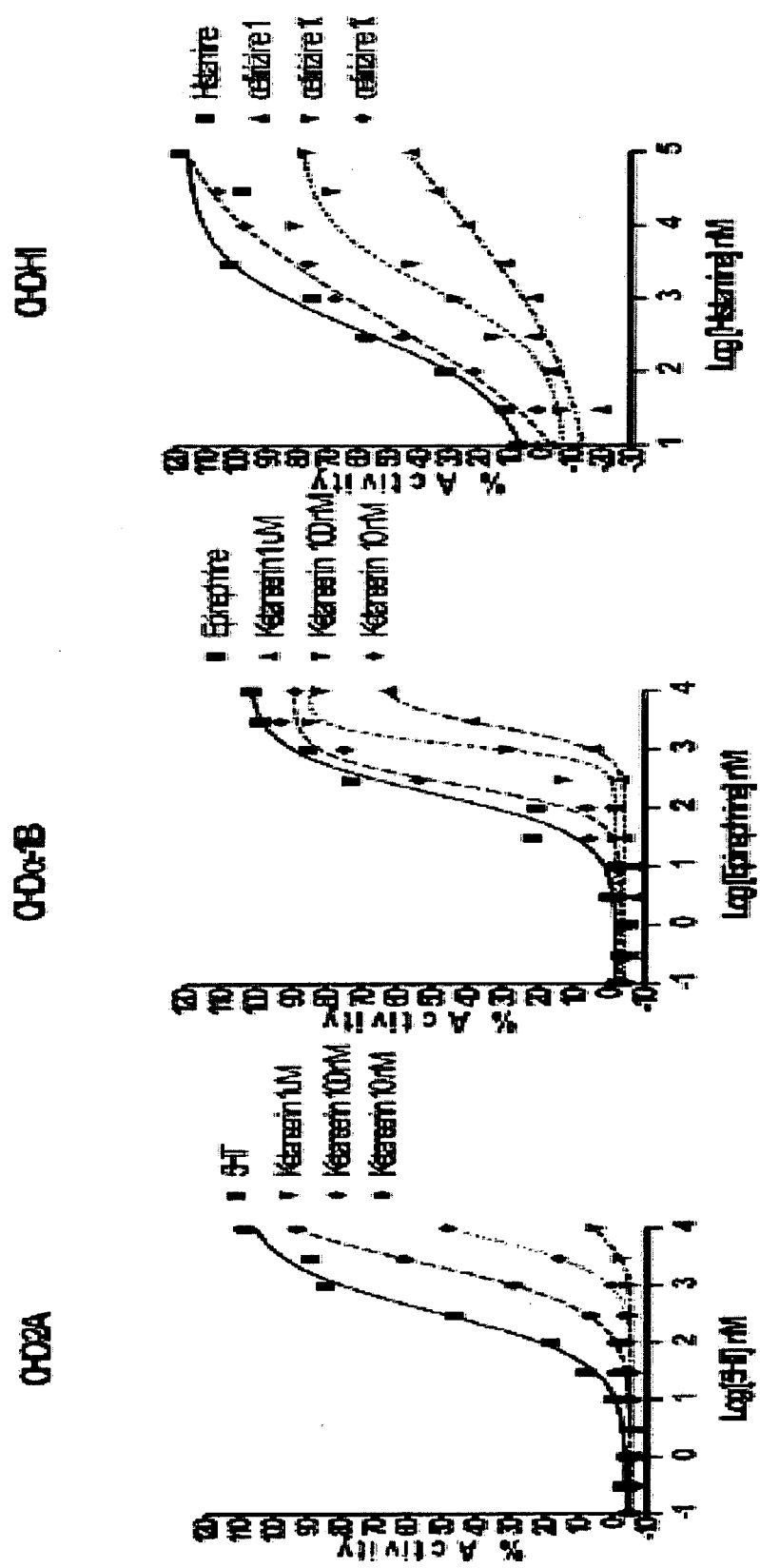
FIG. 5 shows dose response graph of serotonin on CHO-$5HT_{2A}$ cells (in the presence of 10, 100 and 1000 nM Ketanserin), dose response graph of epinephrine on CHO-$\alpha_{1b}$ (in the presence of 10, 100 and 1000 nM Ketanserin) and dose response graph of histamine on CHO-$H_1$ cells (in the presence 10, 100 or 1000 nM Cetirizine). The agonist concentration used was same as in FIG. 3.
Figure 6:
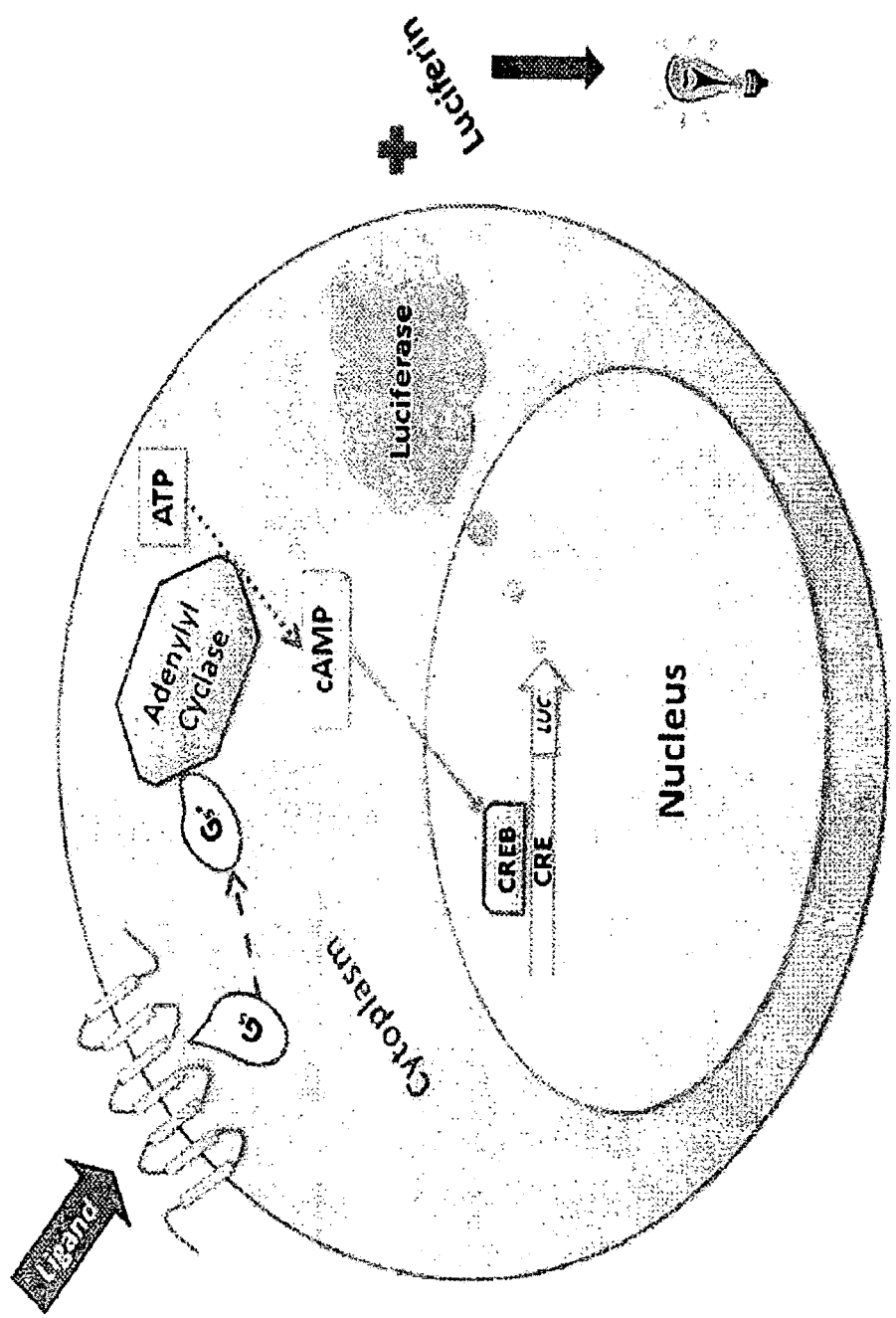
FIG. 6 shows graphical representation of method for screening of $5-HT_{2A}$, histamine H1 or adrenergic alpha 1b receptor compounds.

Ketanserin, mianserin, olanzapine, clozapine and chlorpromazine (each at 10 μM concentrations) fully antagonized the serotonin induced and 5-HT$_{2A}$ mediated induction of luciferase activity in CHO-5HT$_{2A}$ cells. While haloperidol exhibited a limited antagonism, cetirizine did not show any impact on serotonin induced luciferase activity in CHO-5HT$_{2A}$ cells. Risperidone demonstrated an inverse agonism on 5-HT$_{2A}$ receptor and brought down the luciferase activity to less than vehicle control. A treatment of CHO-5HT$_{2A}$ cells with increasing concentrations of serotonin (0.1 to 10,000 nM) in the presence of 0, 10, 100 and 1000 nM ketanserin resulted in a significant right shift in the graph (FIG. 5). The rightward shift in the graph in FIG. 5 was dependent on the concentration of ketanserin used, with maximum shift observed with 1000 nM dose. To better understand the effect of these compounds on serotonin induced luciferase activity in CHO-5HT$_{2A}$ cells, a dose response study was performed. The cells were incubated with the increasing concentrations of above compounds (0.1 to 10,000 nM) along with 10 μM serotonin and luciferase activity was measured. Table 2 provides a pIC$_{50}$ as well as pK$_b$ value for each compound tested in all three cell lines. As evident from Table 2, majority of the compounds demonstrated a potent antagonism to serotonin induced luciferase activity in CHO-5HT$_{2A}$ cells with a pIC$_{50}$ value of close to or less than 7.0 with the exception of cetirizine and haloperidol. Cetirizine and haloperidol exhibited none or partial antagonism to serotonin induced luciferase activity in CHO-2A cells. Serotonin completely displaced ketanserin in CHO-5HT$_{2A}$ cells. Similarly, ketanserin fully displaced serotonin when assayed in the same cell line. All these observations support a competitive and reversible binding of ligands to CHO-5HT$_{2A}$ cells.

Figure 4:
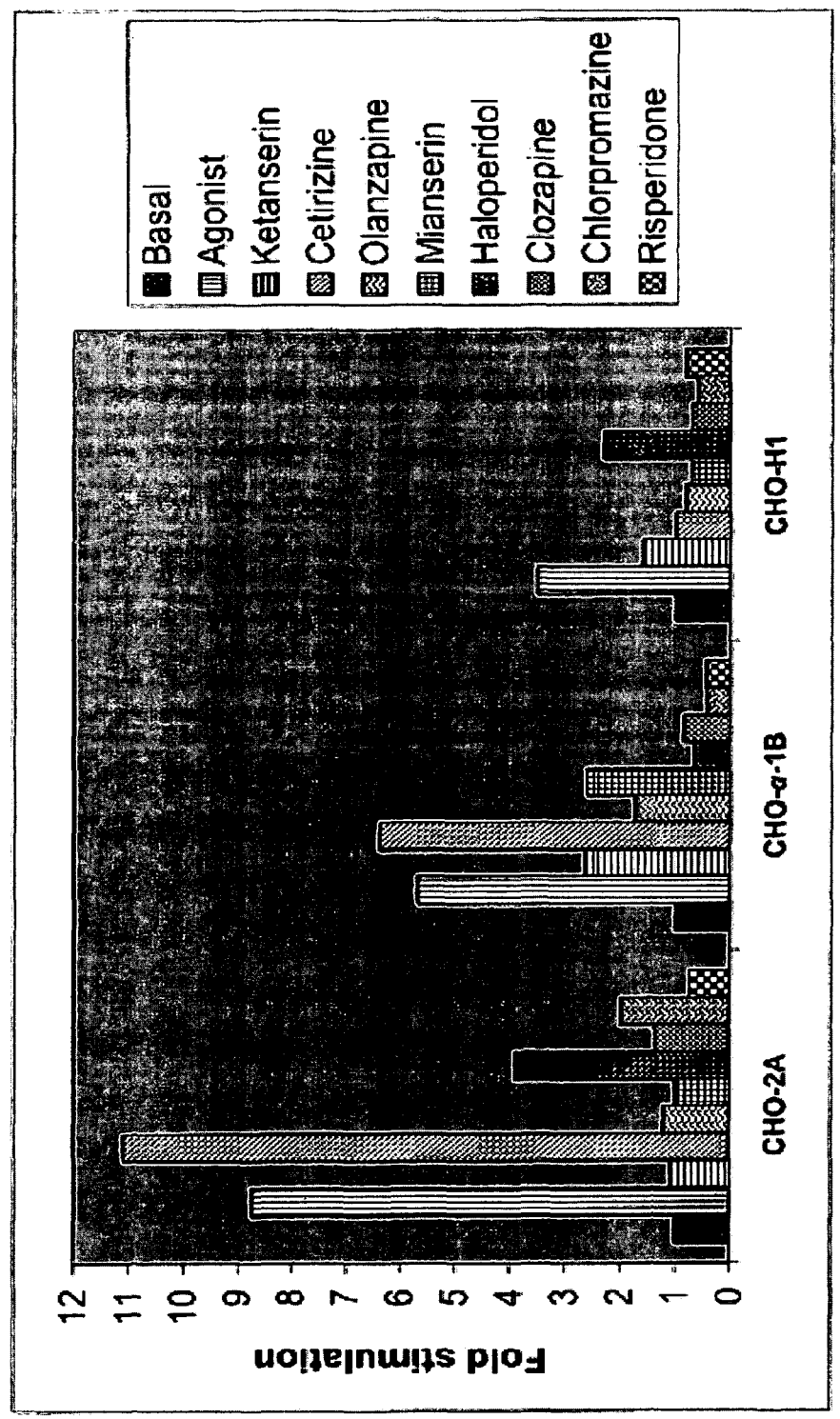
FIG. 4 shows blockade of reporter gene expression by antagonists.

The effect of same set of compounds, tested in CHO-5HT$_{2A}$ cells, was investigated in CHO-α$_{1b}$ cells. Haloperidol, clozapine, chlorpromazine and risperidone (at a concentration of 10 μM) completely blocked the epinephrine induced luciferase activity in the recombinant cells (FIG. 4). In comparison to the above compounds, ketanserin, olanzapine and mianserin showed a limited efficacy, cetirizine did not show any effect on the epinephrine induced luciferase activity in CHO-α$_{1b}$ cells. Chlorpromazine and risperidone demonstrated a potent antagonism to epinephrine induced luciferase activity in CHO-α$_{1b}$ with pIC$_{50}$ values of 6.9 and 7.1 respectively (FIG. 4, Table 2). Rest of the compounds showed a pIC$_{50}$ value of close to or less than 6.0. As expected, cetirizine did not show any antagonism of epinephrine induced luciferase activity. We studied the effect of various concentrations of ketanserin on the level of luciferase activity in CHO-α$_{1b}$ cells upon treatment with increasing concentrations of epinephrine. Selection of ketanserin for this evaluation was guided by the observation that it had limited impact on blocking the epinephrine induced luciferase activity in CHO-α$_{1b}$ cells. As evident from FIG. 5, ketanserin did induce a rightward shift in the graph as compared to control epinephrine treated samples. The extent of rightward shift in curves was dependent on the concentration of ketanserin used with the maximum shift at 1000 nM dose. However, the effect of ketanserin on CHO-α$_{1b}$ cells was milder than on CHO-5HT$_{2A}$ cells which are well in agreement with the fact that it has a higher affinity for human 5-HT$_{2A}$ receptor as compared to alpha 1b receptor. The assay supported a reversible mode of interaction of epinephrine as well as kentanserin to CHO-α$_{1b}$ cells.

CHO-H$_1$ cells were evaluated for the blockade of histamine induced luciferase activity by a defined set of compounds. As evident from FIGS. 2 and 4, CHO-H$_1$ cells exhibited about four fold stimulation of luciferase activity with 10 μM histamine which correlated well with a direct cAMP measurement in CHO cells expressing human histamine H$_1$ receptor reported. Histamine induced luciferase activity was completely blocked by H$_1$ specific antagonist cetirizine (FIG. 4). In addition, all the tested compounds with the exception of haloperidol (at a concentration of 10 μM) blocked the histamine induced luciferase activity to the basal level. Effect of different concentrations of cetirizine on the histamine induced luciferase activity in CHO-H$_1$ cells was investigated. Cetirizine treatment resulted in a rightward shift in the curves plotted with an increasing concentration of histamine (FIG. 5). Cetirizine also demonstrated an inverse agonist property as evident from FIG. 4. Most of the compounds evaluated showed a potent antagonism of histamine induced luciferase activity in CHO-H$_1$ cells in a dose dependent manner. Mianserin demonstrated to be the most potent compound in the assay with a pIC50 value of 8.1. Cetirizine showed a pIC$_{50}$ value of 6.3.

The assay apart from demonstrating various mode of action of a compound to GPCRs can also be utilized to characterize orthosteric or allosteric mode of action of a compound. Furthermore, the reporter gene based functional assay can identify whether a compound interacts with the receptor in a reversible or irreversible manner.

EXAMPLE 6

Once the reporter gene assay was established and detailed pIC$_{50}$ and pK$_b$ values were determined for a number of compounds, it was of interest to measure their binding affinity for the same set of receptors. Although the binding parameters for majority of these compounds are already reported, it was important to evaluate them in parallel with the reporter gene based functional assays.

TABLE 2 pIC$_{50}$ and pK$_b$ values obtained from functional assays

| Compounds | CHO-5HT$_{2A}$ | | CHO-α$_{1b}$ | | CHO-H$_1$ | |
| --- | --- | --- | --- | --- | --- | --- |
| | pIC$_{50}$ | pK$_b$ | pIC$_{50}$ | pK$_b$ | pIC$_{50}$ | pK$_b$ |
| Ketanserin | 7.1 ± 0.2 | 9.0 ± 0.2 | 5.4 ± 0.2 | 7.7 ± 0.2 | 5.9 ± 0.1 | 7.4 ± 0.2 |
| Mianserin | 7.1 ± 0.2 | 8.9 ± 0.04 | 5.0 ± 0.3 | 7.4 ± 0.3 | 8.1 ± 0.04 | 10.1 ± 0.01 |
| Cetirizine | <5 | <5 | <5 | <5 | 6.3 ± 0.2 | 8.4 ± 0.2 |
| Olanzapine | 7.5 ± 0.3 | 9.3 ± 0.1 | 5.7 ± 0.1 | 7.9 ± 0.2 | 7.99 ± 0.3 | 10 ± 0.3 |
| Haloperidol | 5.8 ± 0.4 | 7.5 ± 0.1 | 6.2 ± 0.1 | 8.6 ± 0.1 | 5.4 ± 0.2 | 7.4 ± 0.4 |
| Clozapine | 6.5 ± 0.4 | 8.3 ± 0.2 | 6.0 ± 0.2 | 8.3 ± 0.2 | 7.8 ± 0.3 | 9.8 ± 0.3 |
| Chlorpromazine | 6.9 ± 0.3 | 8.6 ± 0.1 | 6.9 ± 0.05 | 9.3 ± 0.05 | 6.75 ± 0.06 | 8.8 ± 0.2 |
| Risperidone | 8.5 ± 0.3 | 10.3 ± 0.2 | 7.1 ± 0.1 | 9.5 ± 0.1 | 5.9 ± 0.06 | 7.9 ± 0.1 |

Radioligand binding and competition assays were performed with membranes prepared from the recombinant CHO cell lines as described in following three references:
1. Nelson D L, Lucaites V L, Wainscott D B, Glennon R A: Comparison of hallucinogenic phenylisopropylamine binding affinities at cloned human 5-HT$_{2A}$, 5-HT$_{2B}$ and 5-HT$_{2C}$ receptors. Naunyn-Schmiedeberg's Arch Pharmacol 1999, 359: 1-6.
2. Yoshio R, Taniguchi T, Itoh H, Muramatsu I: Affinity of serotonin receptor antagonists and agonists to recombinant and native α1-adrenoreceptor subtypes. Jpn J Pharmacol 2001, 86: 189-195.
3. Ratnala V R P, Swarts H G P, VanOostrum J, Leurs R, DeGroot H J M, Bakker R A, DeGrip W J: Large scale overproduction, functional purification and ligand affinities of his-tagged human histamine H$_1$ receptor. Eur J Biochem 2004, 271:263 6-2646.

All the assays were converted to scintillation proximity assay (SPA) based format. For competition binding assays, 0.1 to 10,000 nM of each compound was incubated with a fixed concentration of the specific radioligands, membrane and SPA beads. For adrenergic alpha$_{1b}$ receptor, 4.0 nM of Prazosin [7-methoxy-$^3$H] was incubated with recombinant membrane and Polylysine (PLL) coated Yitrium silicate (Ysi) SPA beads for three hours at ambient temperature. For, histamine H$_1$ binding assay, 1 nM of Pyrilamine [pyridinyl 5-$^3$H] was incubated with the membrane and Wheat Germ Agglutinin (WGA) coated Polyvinyl Toluene (Pvt) SPA beads for two hours at the ambient temperature. For 5-HT$_{2A}$ binding assay, 3.1 nM Ketanserin Hydrochloride [ethylene-$^3$H] was incubated with the membrane and WGA coated Ysi SPA beads in dark for four hours. After incubation was over, radioactivity was measured in MICROBETA® plate reader (Perkin Elmer). Total binding was determined in the absence of any ligands whereas non-specific binding was determined to be counts obtained in the presence of excess amount of specific ligands. Specific activity was calculated from the differences between total and non-specific counts.

Radioligand binding assay using SPA beads were performed to determine the pK$_i$ values for specific compounds. The binding experiment was performed thrice and average values are presented in Table 3. As evident, all the compounds showed a pK$_i$ value which well correlates with the already reported values. These compounds also demonstrated target selectivity as reported earlier (www.iuphar-db.org/GPCR/ReceptorFamiliesForward). Serotonin exhibited a pK$_i$ value of 6.8 to 5-HT$_{2A}$ receptor but did not show any binding to alpha$_{1b}$ and H$_1$ receptors. Similarly, epinephrine showed strong binding to alpha 1b receptor with a pK$_a$ value of 6.4 but a weak affinity for 5-HT$_{2A}$ and no binding to H$_1$ receptors. The pK$_i$ value determined is well in agreement with the published value. Histamine did not show any binding to either 5-HT$_{2A}$ or alpha$_{1b}$ receptors while giving a pK$_i$ value of 5.9 with H$_1$ receptor which is again well in agreement with previously reported values. Ceterizine demonstrated a selective binding to human H$_1$ receptor with a pK$_b$ value of 7.7 and no affinity to 5-HT$_{2A}$ or H$_1$ receptors. Clozapine, mianserin, ketanserin and olanzapine showed varying degree of binding to all the above receptors (Table 3).

TABLE 3 pK$_i$ values determined from radioligand binding assays

| Compounds/Targets | 5-HT$_{2A}$ | α$_{1b}$ | H$_1$ |
|---|---|---|---|
| Serotonin | 6.8 ± 0.02 | <5 | <5 |
| Epinephrine | 5.1 ± 0.1 | 6.4 ± 0.1 | <5 |
| Histamine | <5 | <5 | 5.9 ± 0.01 |
| Clozapine | 7.8 ± 0.1 | 7.2 ± 0.2 | 8.8 ± 0.1 |
| Mianserin | 8.2 ± 0.2 | 6.9 ± 0.1 | 9.7 ± 0.1 |
| Ketanserin | 8.9 ± 0.1 | 7.2 ± 0.1 | 7.7 ± 0.03 |
| Olanzapine | 7.5 ± 0.1 | 6.5 ± 0.1 | 8.6 ± 0.1 |
| Cetirizine | <5 | <5 | 7.7 ± 0.1 |

EXAMPLE 7 pK$_i$ and pK$_b$ are derived parameters from pIC$_{50}$ value which are determined by binding assays and functional assays respectively. As the pIC$_{50}$ value for the same ligand and receptor combination may vary depending on the amount of radioligand used in the binding assay or amount of agonist used in the functional assay, derived pK$_i$ and pK$_b$ values demonstrate a constant parameter for a specific compound. Thus, we compared the pK$_i$ and pK$_b$ values for specific compounds derived from radioligand binding assay or cell based function assay. For an agonist, pEC$_{50}$ value derived from the functional assay is compared with the pK$_i$ value determined from the binding assay. As evident from Table 4, majority of the compounds showed a good correlation between pK$_b$ or pEC$_{50}$ values derived from the functional assay and pK$_i$ values generated from the radioligand binding assay.

TABLE 4 pEC$_{50}$, pK$_i$ and pK$_b$ value comparison

| | 5-HT$_{2A}$ | | α$_{1b}$ | | H$_1$ | |
|---|---|---|---|---|---|---|
| Compounds/Targets | pEC$_{50}$ or pK$_b$ | pK$_i$ | pEC$_{50}$ or pK$_b$ | pK$_i$ | pEC$_{50}$ or pK$_b$ | pK$_i$ |
| Serotonin | 6.6 ± 0.1 | 6.8 ± 0.02 | <5 | <5 | <5 | <5 |
| Epinephrine | <5 | 5.1 ± 0.1 | 7.0 ± 0.3 | 6.4 ± 0.1 | <5 | <5 |
| Histamine | <5 | <5 | <5 | <5 | 6.0 ± 0.1 | 5.9 ± 0.01 |
| Clozapine | 8.3 ± 0.2 | 7.8 ± 0.1 | 8.3 ± 0.2 | 7.2 ± 0.2 | 9.8 ± 0.3 | 8.8 ± 0.1 |
| Mianserin | 8.9 ± 0.04 | 8.2 ± 0.2 | 7.4 ± 0.3 | 6.9 ± 0.1 | 10.1 ± 0.01 | 9.7 ± 0.1 |
| Ketanserin | 9.0 ± 0.2 | 8.9 ± 0.1 | 7.7 ± 0.2 | 7.2 ± 0.1 | 7.4 ± 0.2 | 7.7 ± 0.03 |
| Olanzapine | 9.3 ± 0.1 | 7.5 ± 0.1 | 7.9 ± 0.2 | 6.5 ± 0.1 | 10 ± 0.3 | 8.6 ± 0.1 |
| Cetirizine | <5 | <5 | <5 | <5 | 8.4 ± 0.2 | 7.7 ± 0.1 |

We claim:

1. An assay method for screening for antagonists and agonists of 5-HT$_{2A}$ receptor, histamine H1 receptor or adrenergic alpha 1b receptor by a reporter gene based assay in a microtitre plate comprising:

a) transfecting chinese hamster ovary (CHO) cells with a specific G-Protein Coupled Receptor (GPCR) coupled to a G protein containing Gαq subunit construct, wherein the specific GPCR is selected from 5-HT$_{2A}$ receptor, Histamine H1 receptor and adrenergic alpha 1b receptor along with excess of cAMP response element luciferase (CRE-luc) reporter gene with 1-Propanaminium, N-(3-[(4[(3-aminopropyl) amino) butyl) amino) propyl) amino)-3-oxopropyl)-N,N-dimethyl-2,3-bis(((9z)-1-oxo-9-octadecenyl)oxy)-, 2,2,2-trifluoroacetate (1:1), mixt. with 1-(((2-aminoethoxy) hydroxyphosphinyl)oxy)methyl)-1,2-ethanediyl di-(9z)-9-octadecenoate and culturing the resultant recombinant CHO cells in a suitable medium containing a selection of suitable antibiotics;

b) selecting individual colonies of recombinant CHO cells exhibiting maximum luciferase activity to both forskolin and an agonist of said specific GPCR and analyzing the expression of said specific GPCR;

c) plating and culturing the selected recombinant CHO cells in a microtitre plate;
d) incubating said cultured, recombinant CHO cells with increasing concentrations of a test compound at 37° C. in $CO_2$ incubator and evaluating the effect of the test compound as an antagonist or agonist of said specific GPCR;
e) after incubation of the cells is over, removing the medium, washing the cells with buffer and lysing the cells with lysis buffer; and
f) measuring the CRE-Luc reporter gene activity in individual wells of the microtitre plate.

2. The method as claimed in claim 1, wherein said luciferase reporter gene constructs is three fold in excess.

3. The method as claimed in claim 1, wherein said microtitre plate is used for high throughput screening.

* * * * *